US011291511B2

(12) United States Patent
Moctezuma de la Barrera et al.

(10) Patent No.: US 11,291,511 B2
(45) Date of Patent: Apr. 5, 2022

(54) ROBOTIC SYSTEMS AND METHODS FOR CONTROLLING A TOOL REMOVING MATERIAL FROM A WORKPIECE

(71) Applicant: MAKO Surgical Corp., Ft. Lauderdale, FL (US)

(72) Inventors: José Luis Moctezuma de la Barrera, Freiburg (DE); David Gene Bowling, Los Ranchos De Albuquerque, NM (US); Donald W. Malackowski, Schoolcraft, MI (US); Patrick Roessler, Merzhausen (DE); Joel N. Beer, Albuquerque, NM (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 172 days.

(21) Appl. No.: 16/139,985

(22) Filed: Sep. 24, 2018

(65) Prior Publication Data
US 2019/0021802 A1     Jan. 24, 2019

Related U.S. Application Data

(63) Continuation of application No. 15/195,039, filed on Jun. 28, 2016, now Pat. No. 10,117,713.
(Continued)

(51) Int. Cl.
*A61B 34/30*     (2016.01)
*A61B 17/16*     (2006.01)
(Continued)

(52) U.S. Cl.
CPC .......... *A61B 34/30* (2016.02); *A61B 17/1626* (2013.01); *A61B 34/10* (2016.02);
(Continued)

(58) Field of Classification Search
CPC ......... A61B 34/10; A61B 34/20; A61B 34/30; A61B 34/32; A61B 90/39;
(Continued)

(56) References Cited

U.S. PATENT DOCUMENTS

| 4,672,550 A | 6/1987 | Winterbottom |
| 5,408,409 A | 4/1995 | Glassman et al. |

(Continued)

FOREIGN PATENT DOCUMENTS

| DE | 19954005 A1 | 6/2001 |
| WO | 2009092164 A1 | 7/2009 |
| WO | 2016115306 A1 | 7/2016 |

OTHER PUBLICATIONS

Choi et al., "VISBONE: 3D Visualization of Bone Mineral Density", Pacific Conference on Computer Graphics and Applications, pp. 138-146, IEEE Computer Society, 1999, 9 pages.
(Continued)

*Primary Examiner* — Rachid Bendidi
(74) *Attorney, Agent, or Firm* — Howard & Howard Attorneys PLLC (57) ABSTRACT

A method of operating a robotic system to efficiently remove material from a workpiece based on a density distribution of the material of the workpiece. The density distribution of the material of the workpiece is determined from a three-dimensional representation and evaluated by classifying the plurality of points or voxels into a first density classification and a second density classification. A navigation computer generates a first tool path and a second tool path for the tool based on the evaluated density distribution. The first tool path is associated with the first density classification, and the second tool path is associated with the second density classification. The position of the tool relative to the workpiece is tracked with a navigation computer and controlled with a manipulator controller based on the generated tool
(Continued)

path to remove material along the first tool path, and remove material along the second tool path.

20 Claims, 7 Drawing Sheets

Related U.S. Application Data (60) Provisional application No. 62/187,481, filed on Jul. 1, 2015.

(51) Int. Cl.
| | |
|---|---|
| *B25J 11/00* | (2006.01) |
| *A61B 34/20* | (2016.01) |
| *B25J 9/16* | (2006.01) |
| *A61B 34/10* | (2016.01) |
| *A61B 34/32* | (2016.01) |
| *A61B 90/00* | (2016.01) |
| *G05B 19/4093* | (2006.01) |
| *A61B 17/17* | (2006.01) |

(52) U.S. Cl.
CPC ............ *A61B 34/20* (2016.02); *A61B 34/32* (2016.02); *A61B 90/39* (2016.02); *B25J 9/1664* (2013.01); *B25J 9/1671* (2013.01); *B25J 11/0055* (2013.01); *A61B 17/1764* (2013.01); *A61B 2034/105* (2016.02); *A61B 2034/2051* (2016.02); *A61B 2034/2055* (2016.02); *A61B 2034/2057* (2016.02); *A61B 2034/2063* (2016.02); *A61B 2090/3945* (2016.02); *G05B 19/40937* (2013.01); *G05B 2219/35021* (2013.01); *G05B 2219/45168* (2013.01)

(58) Field of Classification Search
CPC .... A61B 2034/2063; A61B 2034/2057; A61B 2034/2051; A61B 2034/105; A61B 2034/3945; A61B 17/1764; B25J 11/0055; B25J 9/1664; G05B 2219/45168; G05B 2219/35021; G05B 19/40937

See application file for complete search history.

(56) References Cited

U.S. PATENT DOCUMENTS

| | | |
|---|---|---|
| 5,548,694 A | 8/1996 | Frisken |
| 6,665,948 B1 | 12/2003 | Kozin et al. |
| 7,055,601 B2 | 6/2006 | Barrow |
| 7,725,162 B2 | 5/2010 | Malackowski et al. |
| 8,219,352 B2 | 7/2012 | Taguchi et al. |
| 8,649,577 B1 | 2/2014 | Arnold |
| 8,657,821 B2 | 2/2014 | Palermo |
| 9,008,757 B2 | 4/2015 | Wu |
| 9,119,655 B2 | 9/2015 | Bowling et al. |
| 9,381,085 B2 | 7/2016 | Axelson, Jr. et al. |
| 10,117,713 B2 | 11/2018 | Moctezuma de la Barrera et al. |
| 2004/0010190 A1 | 1/2004 | Shahidi |
| 2011/0015649 A1 | 1/2011 | Anvari et al. |
| 2011/0112397 A1 | 5/2011 | Shen |
| 2011/0306985 A1* | 12/2011 | Inoue ..................... G06T 15/08 606/130 |
| 2012/0059378 A1 | 3/2012 | Farrell |
| 2014/0039314 A1 | 2/2014 | Stoianovici et al. |
| 2014/0039517 A1 | 2/2014 | Bowling et al. |
| 2014/0200621 A1 | 7/2014 | Malackowski et al. |
| 2015/0157419 A1 | 6/2015 | Bell |
| 2015/0366629 A1 | 12/2015 | Bowling |
| 2018/0263697 A1* | 9/2018 | Eskesen ............ A61B 17/1703 |

OTHER PUBLICATIONS

English language abstract and machine-assisted translation of DE19954005 extracted from espacenet.com Oct. 14, 2016, 5 pages.
Ferretti, "Peripheral Quantitative Computed Tomography (pQCT) for Evaluating Structural and Mechanical Properties of Small Bone", Practical Guide for Mechanical Testing of Bone, 1999, CRC Press, Boca Raton, FL, USA, 32 pages.
International Search Report and Written Opinion for PCT/US2016/039842 dated Sep. 29, 2016, 15 pages.
Lin et al., "Collision Detection Between Geometric Models: A Survey", In Proc. of IMA Conference on Mathematics of Surfaces, University of North Carolina at Chapel Hill, Jun. 1998, 20 pages.
Salisbury et al., "Haptic Rendering: Introductory Concepts", pp. 24-32., IEEE Computer Graphics and Applications Mar./Apr. 2004, IEEE Computer Society, 2004, 9 pages.

\* cited by examiner

ROBOTIC SYSTEMS AND METHODS FOR CONTROLLING A TOOL REMOVING MATERIAL FROM A WORKPIECE

RELATED APPLICATIONS

This application is a continuation of co-pending U.S. application Ser. No. 15/195,039, filed on Jun. 28, 2016, which claims the benefit of and priority to U.S. Provisional Patent Application No. 62/187,481, filed on Jul. 1, 2015, the entire contents of each are hereby incorporated by reference herein.

TECHNICAL FIELD

The present invention relates generally to robotic systems and methods for controlling a tool removing material from a workpiece.

BACKGROUND

Robotic systems having tools for removing material from workpieces are well known. One such system is a machining system having one or more cutting tools for forming a workpiece into a desired shape by cutting material from the workpiece. In many cases, the workpiece is generally homogeneous and has a consistent density throughout. Owing to the homogeneous nature of the workpiece, a constant feed rate (e.g., velocity), a uniform tool path, and a constant rotational speed of the cutting tool are often employed and provide efficient, accurate cutting of the material from the workpiece. The feed rate, tool path, and rotational speed employed in these types of systems may be based on characteristics of the material being cut. For example, the feed rate of the cutting tool may be set relatively slower for workpieces formed of denser material. Workpieces formed of denser materials often require slower feed rates in order to maintain consistent cutting accuracy. Otherwise, if the feed rate is set too high for these workpieces, errors may occur as a result of unexpected deflections of the tool, which yields inaccurate cuts. Conversely, for materials having lower densities, relatively faster feed rates may be appropriate, resulting in quicker operating times, while maintaining desired cutting accuracy. Similarly, the tool path of the cutting tool may be set relatively shallower for workpieces formed of denser material in order to reduce heat generation at a tool/workpiece interface. Otherwise, the workpiece may reach temperatures that degrade or damage the workpiece. Likewise, rotational speeds of the cutting tool may be adjusted for different materials to reduce the generation of heat and improve cutting efficiency.

Workpieces such as bone, however, are often non-homogenous and have varying density distributions throughout their volume. As a result, applying a constant feed rate, a uniform tool path, and a constant rotational speed may not be efficient for all portions of the workpiece. Accordingly, there is a need in the art for systems and methods to assist in controlling tools for such non-homogeneous workpieces.

SUMMARY

This Summary introduces a selection of concepts in a simplified form that are further described below in the Detailed Description below. This Summary is not intended to limit the scope of the claimed subject matter nor identify key features or essential features of the claimed subject matter.

One example of a method of operating a robotic system to efficiently remove material from a workpiece based on a density distribution of the material of the workpiece is provided. The robotic system may include a manipulator, a tool coupled to the manipulator to remove material from a workpiece, a manipulator controller coupled to the manipulator, and a navigation computer. A density distribution of material of the workpiece is determined from a three-dimensional representation of the workpiece comprising a plurality of points or voxels. The density distribution is evaluated by classifying the plurality of points or voxels into a first density classification and a second density classification different than the first density classification. The navigation computer generates a first tool path and a second tool path for the tool based on the evaluated density distribution of the workpiece. The first tool path is associated with the first density classification, and the second tool path is associated with the second density classification. The navigation computer tracks a position of the tool relative to the workpiece as the tool moves relative to the workpiece. The position of the tool relative to the workpiece is controlled with the manipulator controller based on the generated tool path to remove at least a portion of the material along the first tool path, and remove at least a portion of the material along the second tool path.

The system and methods may exhibit advantages and provide technical solutions other than those described herein.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
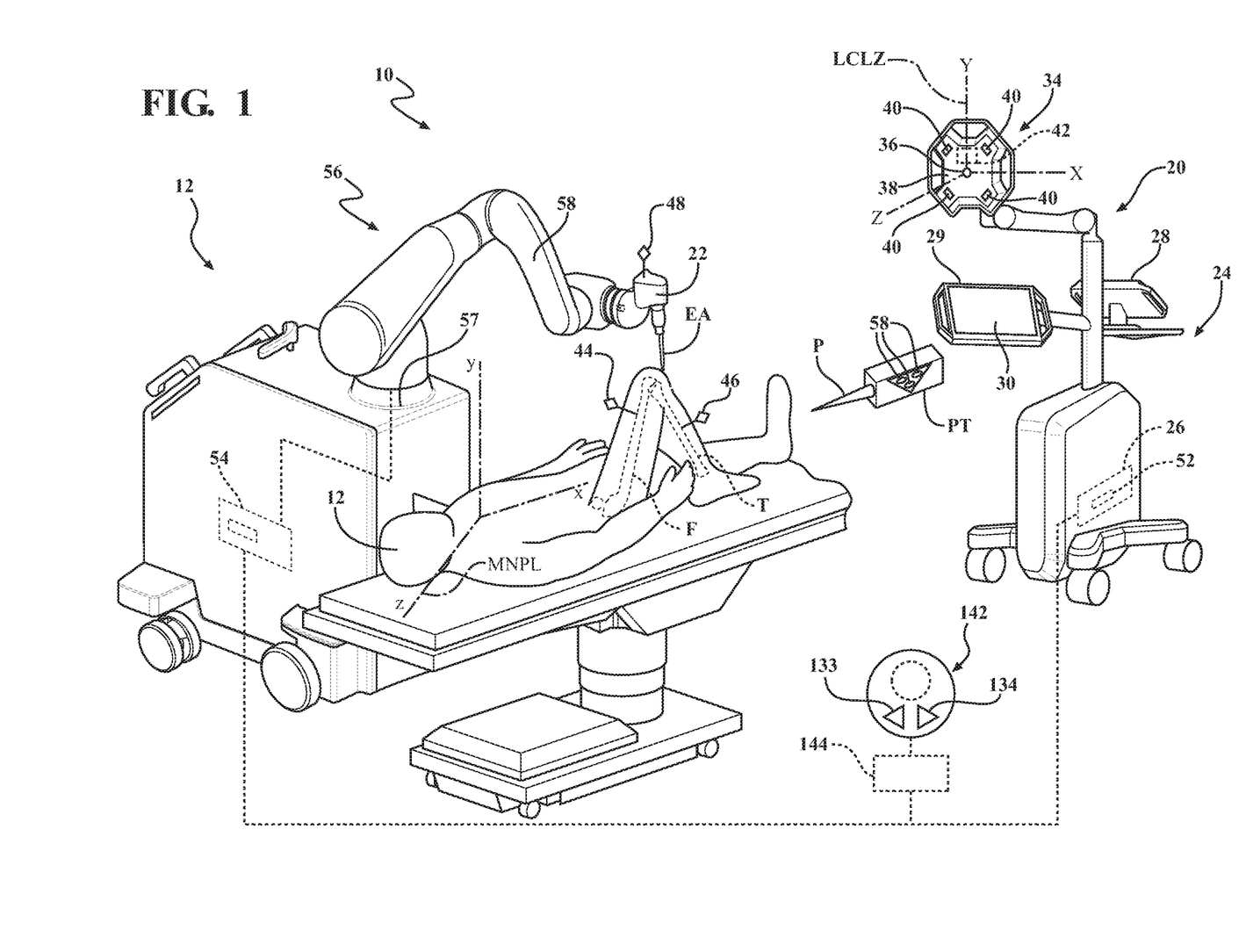
FIG. 1 is a perspective view of a material removal system being used to remove material from a workpiece.

Referring to FIG. 1 a material removal system 10 for removing material from a workpiece is illustrated. The material removal system 10 is shown in a surgical setting such as an operating room of a medical facility. In the embodiment shown, the material removal system 10 includes a machining station 12 and a guidance station 20. The guidance station 20 is set up to track movement of various objects in the operating room. Such objects include, for example, a surgical tool 22, a femur F of a patient, and a tibia T of the patient. The guidance station 20 tracks these objects for purposes of displaying their relative positions and orientations to the surgeon and, in some cases, for purposes of controlling or constraining movement of the surgical tool 22 relative to virtual cutting boundaries associated with the femur F and tibia T.

The guidance station 20 includes a computer cart assembly 24 that houses a navigation computer 26. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices such as a keyboard and mouse can be used to input information into the navigation computer 26 or otherwise select/control certain aspects of the navigation computer 26. Other input devices are contemplated including a touch screen 30 or voice-activation.

A localizer 34 communicates with the navigation computer 26. In the embodiment shown, the localizer 34 is an optical localizer and includes a camera unit 36. Other types of localizers are also contemplated, including localizers that employ ultrasound, radio frequency (RF) signals, electromagnetic fields, and the like. The camera unit 36 has an outer casing 38 that houses one or more optical position sensors 40. In some embodiments at least two optical sensors 40 are employed, preferably three or four. The optical sensors 40 may be three separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 with a field of view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation computer 26.

Position and orientation signals and/or data are transmitted to the navigation computer 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The navigation computer 26 can be a personal computer or laptop computer. Navigation computer 26 has the display 28, central processing unit (CPU) and/or other processors, memory (not shown), and storage (not shown). The navigation computer 26 is loaded with software as described below. The software converts the signals received from the camera unit 36 into data representative of the position and orientation of the objects being tracked.

Guidance station 20 is operable with a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. patent application Ser. No. 14/156,856, filed on Jan. 16, 2014, entitled, "Navigation Systems and Methods for Indicating and Reducing Line-of-Sight Errors," hereby incorporated by reference herein. In additional embodiments, a tracker (not shown) is attached to the patella to track a position and orientation of the patella. In yet further embodiments, the trackers 44, 46 could be mounted to other tissue types or parts of the anatomy.

A tool tracker 48 is firmly attached to the surgical tool 22. The tool tracker 48 may be integrated into the surgical tool 22 during manufacture or may be separately mounted to the surgical tool 22 in preparation for surgical procedures. The working end of the surgical tool 22, which is being tracked by virtue of the tool tracker 48, may be an energy applicator EA such as a rotating bur, saw blade, electrical ablation device, or the like. The energy applicator EA may be a separate component such as a bur, saw blade, ablator, or the like that is releasably connected to a handpiece of the surgical tool 22 or may be integrally formed with the handpiece.

The trackers 44, 46, 48 can be battery powered with an internal battery or may have leads to receive power through the navigation computer 26, which, like the camera unit 36, preferably receives external power.

In the embodiment shown, the surgical tool 22 is attached to a manipulator 56 of the machining station 12. Such an arrangement is shown in U.S. Pat. No. 9,119,655, entitled, "Surgical Manipulator Capable of Controlling a Surgical Instrument in Multiple Modes," the disclosure of which is hereby incorporated by reference.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

Figure 2:
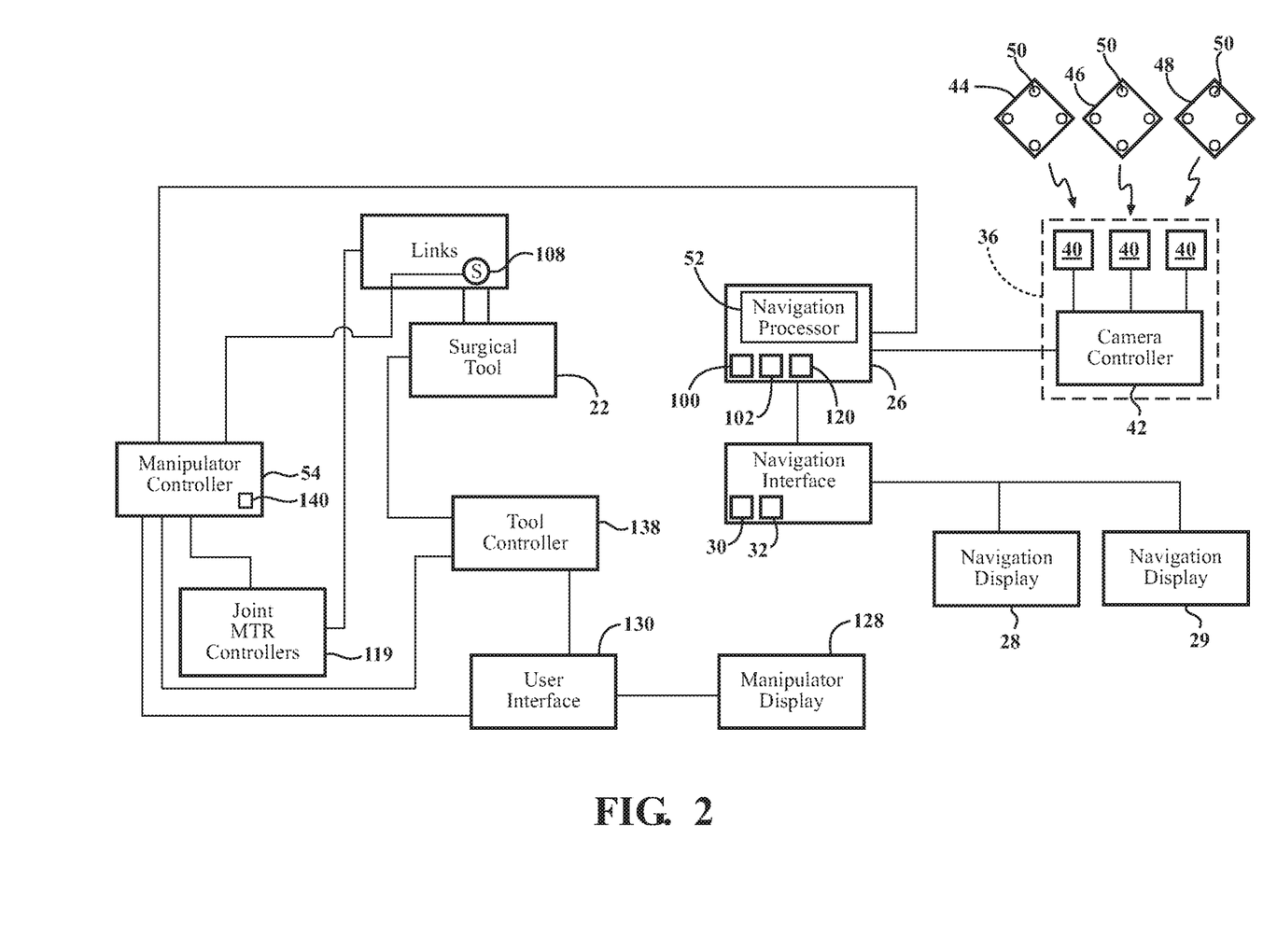
FIG. 2 is a schematic view the material removal system.

Referring to FIG. 2, each of the LEDs 50 are connected to a tracker controller (not shown) located in a housing of the associated tracker 44, 46, 48 that transmits/receives data to/from the navigation computer 26. In one embodiment, the tracker controllers transmit data on the order of several Megabytes/second through wired connections with the navigation computer 26. In other embodiments, a wireless connection may be used. In these embodiments, the navigation computer 26 has a transceiver (not shown) to receive the data from the tracker controller.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

In some embodiments, the trackers 44, 46, 48 also include a gyroscope sensor and accelerometer, such as the trackers shown in U.S. patent application Ser. No. 14/035,207, filed on Sep. 24, 2013, entitled, "Navigation System Including Optical and Non-Optical Sensors," hereby incorporated by reference.

The navigation computer 26 includes a navigation processor 52. It should be understood that the navigation processor 52 could include one or more processors to control operation of the navigation computer 26. The processors can be any type of microprocessor or multi-processor system. The term processor is not intended to limit the scope any embodiment to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34.

Prior to the start of the surgical procedure, additional data are loaded into the navigation processor 52. Based on the position and orientation of the trackers 44, 46, 48 and the previously loaded data, navigation processor 52 determines the position of the working end of the surgical tool 22 (e.g., the centroid of a surgical bur) and the orientation of the surgical tool 22 relative to the tissue against which the working end is to be applied. In some embodiments, navigation processor 52 forwards these data to a manipulator controller 54. The manipulator controller 54 can then use the data to control the manipulator 56 as described in U.S. Pat. No. 9,119,655, entitled, "Surgical Manipulator Capable of Controlling a Surgical Instrument in Multiple Modes," the disclosure of which is hereby incorporated by reference.

In one embodiment, the manipulator 56 is controlled to stay within a preoperatively defined boundary set by the surgeon, which defines the material of the femur F and tibia T to be removed by the surgical tool 22. The boundary may be defined within a virtual model of the femur F and tibia T and be represented as a mesh surface, constructive solid geometry (CSG), voxels, or other boundary representation techniques.

The navigation processor 52 also generates image signals that indicate the relative position of the working end to the tissue. These image signals are applied to the displays 28, 29. Displays 28, 29, based on these signals, generate images that allow the surgeon and staff to view the relative position of the working end to the surgical site. The displays, 28, 29, as discussed above, may include a touch screen or other input/output device that allows entry of commands.

Figure 3:
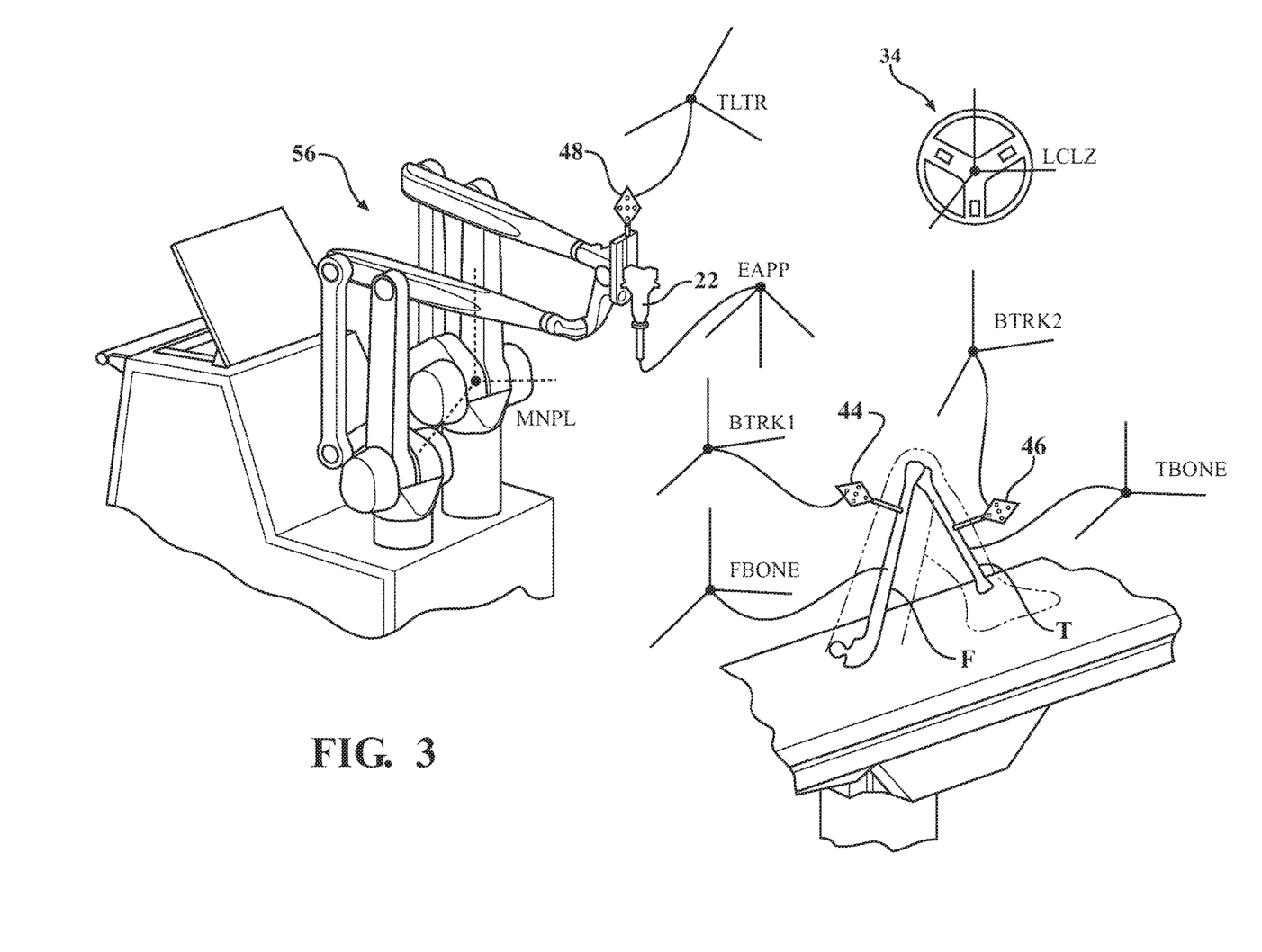
FIG. 3 is schematic view of the coordinate systems used in the material removal system.

Referring to FIG. 3, tracking of objects is generally conducted with reference to a localizer coordinate system LCLZ. The localizer coordinate system has an origin and an orientation (a set of x, y, and z axes). During the procedure one goal is to keep the localizer coordinate system LCLZ in a known position. An accelerometer (not shown) mounted to the camera unit 36 may be used to track sudden or unexpected movement of the localizer coordinate system LCLZ, as may occur when the camera unit 36 is inadvertently bumped by surgical personnel.

Each tracker 44, 46, 48 and object being tracked also has its own coordinate system separate from the localizer coordinate system LCLZ. Components of the guidance station 20 that have their own coordinate systems are the bone trackers 44, 46 and the tool tracker 48. These coordinate systems are represented as, respectively, bone tracker coordinate systems BTRK1, BTRK2, and tool tracker coordinate system TLTR.

Guidance station 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TBONE using well known methods in the art. These images are fixed in the femur coordinate system FBONE and tibia coordinate system TBONE. As an alternative to taking pre-operative images, plans for treatment can be developed in the operating room (OR) from kinematic studies, bone tracing, and other methods.

During an initial phase of the procedure, the bone trackers 44, 46 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIGS. 1 and 2), such as disclosed in U.S. Pat. No. 7,725,162 to Malackowski, et al., hereby incorporated by reference, having its own tracker PT (see FIG. 1), may be used to register the femur coordinate system FBONE and tibia coordinate system TBONE to the bone tracker coordinate systems BTRK1 and BTRK2, respectively. Given the fixed relationship between the bones and their bone trackers 44, 46, positions and orientations of the femur F and tibia T in the femur coordinate system FBONE and tibia coordinate system TBONE can be transformed to the bone tracker coordinate systems BTRK1 and BTRK2 so the camera unit 36 is able to track the femur F and tibia T by tracking the bone trackers 44, 46. These pose-describing data are stored in memory integral with both manipulator controller 54 and navigation processor 52.

The working end of the surgical tool 22 (also referred to as energy applicator distal end) has its own coordinate system EAPP. The origin of the coordinate system EAPP may represent a centroid of a surgical cutting bur, for example. The pose of coordinate system EAPP is fixed to the pose of tool tracker coordinate system TLTR before the procedure begins. Accordingly, the poses of these coordinate systems EAPP, TLTR relative to each other are determined. The pose-describing data are stored in memory integral with both manipulator controller 54 and navigation processor 52.

Referring to FIG. 2, a localization engine 100 is a software module that can be considered part of the guidance station 20. Components of the localization engine 100 run on navigation processor 52. In some embodiments, the localization engine 100 may run on the manipulator controller 54.

Localization engine 100 receives as inputs the optically-based signals from the camera controller 42 and, in some embodiments, the non-optically based signals from the tracker controller 62. Based on these signals, localization engine 100 determines the pose of the bone tracker coordinate systems BTRK1 and BTRK2 in the localizer coordinate system LCLZ. Based on the same signals received for the tool tracker 48, the localization engine 100 determines the pose of the tool tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor

52. Coordinate transformer 102 references the data that defines the relationship between the pre-operative images of the patient and the bone trackers 44, 46. Coordinate transformer 102 also stores the data indicating the pose of the working end of the surgical tool 22 relative to the tool tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of both the coordinate system EAPP, and the bone coordinate systems, FBONE and TBONE to the localizer coordinate system LCLZ.

As a result, coordinate transformer 102 generates data indicating the position and orientation of the working end of the surgical tool 22 relative to the tissue (e.g., bone) against which the working end is applied. Image signals representative of these data are forwarded to displays 28, 29 enabling the surgeon and staff to view this information. In certain embodiments, other signals representative of these data can be forwarded to the manipulator controller 54 to guide the manipulator 56 and corresponding movement of the surgical tool 22.

In the embodiment shown in FIG. 1, the surgical tool 22 forms part of an end effector of the manipulator 56. The manipulator 56 has a base 57, a plurality of links 58 extending from the base 57, and a plurality of active joints (not numbered) for moving the surgical tool 22 with respect to the base 57. The links 58 may form a serial arm structure as shown in FIG. 1, a parallel arm structure as shown in FIG. 3, or other suitable structure. The manipulator 56 has the ability to operate in a manual mode in which a user grasps the end effector of the manipulator 56 in order to cause movement of the surgical tool 22 (e.g., directly, through force/torque sensor measurements that cause active driving of the manipulator 56, or otherwise) or a semi-autonomous mode in which the surgical tool 22 is moved by the manipulator 56 along a predefined tool path (e.g., the active joints of the manipulator 56 are operated to move the surgical tool 22 without requiring force/torque on the end effector from the user). An example of operation in a semi-autonomous mode is described in U.S. Pat. No. 9,119,655, entitled, "Surgical Manipulator Capable of Controlling a Surgical Instrument in Multiple Modes," the disclosure of which is hereby incorporated by reference. A separate tracker (not shown) may be attached to the base 57 of the manipulator 56 to track movement of the base 57.

In one embodiment, when the manipulator 56 is operated in the semi-autonomous mode, the manipulator 56 is capable of moving the surgical tool 22 free of operator assistance. Free of operator assistance may mean that an operator/user does not physically contact the surgical tool 22 to move the surgical tool 22. Instead, the operator may use some form of remote control to control starting and stopping of movement. For example, the operator may hold down a button of the remote control to start movement of the surgical tool 22 and release the button to stop movement of the surgical tool 22.

In the manual mode, in one embodiment, the operator physically contacts the end effector to cause movement of the surgical tool 22, as described in U.S. Pat. No. 9,119,655, entitled, "Surgical Manipulator Capable of Controlling a Surgical Instrument in Multiple Modes," the disclosure of which is hereby incorporated by reference.

The manipulator controller 54 can use the position and orientation data of the surgical tool 22 and the patient's anatomy to control the manipulator 56 as described in U.S. Pat. No. 9,119,655, entitled, "Surgical Manipulator Capable of Controlling a Surgical Instrument in Multiple Modes," the disclosure of which is hereby incorporated by reference.

The manipulator controller 54 may have a central processing unit (CPU) and/or other manipulator processors, memory (not shown), and storage (not shown). The manipulator controller 54, also referred to as a manipulator computer, is loaded with software as described below. The manipulator processors could include one or more processors to control operation of the manipulator 56. The processors can be any type of microprocessor, multi-processor, and/or multi-core processing system. The term processor is not intended to limit any embodiment to a single processor.

Figure 4:
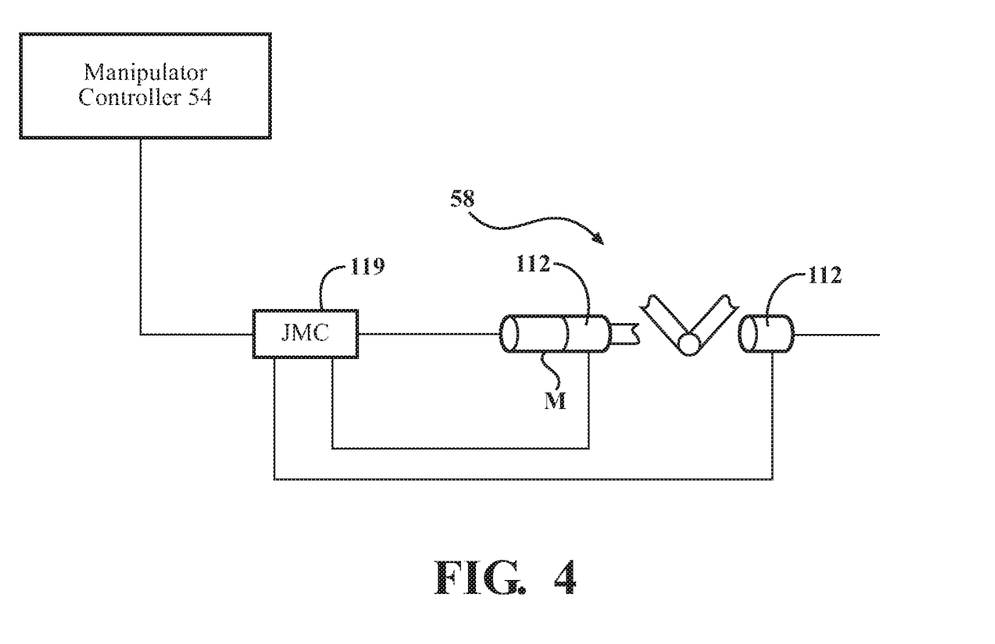
FIG. 4 is a schematic view of joint motor controllers and sensors.

Referring to FIG. 4, a plurality of position sensors 112 are associated with the actuators (e.g., motors M) of the manipulator 56 and/or links 58 being moved by the actuators (only one pair shown, but each actuator and associated link 58 of the manipulator 56 may have their own associated position sensors 112). In one embodiment, the position sensors 112 are encoders. The position sensors 112 may be any suitable type of encoder, such as rotary encoders, e.g., absolute encoders. The position sensors 112 monitor the angular position of the actuators and/or the angular position of the driven links 58 of the manipulator 56. In some embodiments, the manipulator 56 includes a serial arm structure with six position sensors 112 at six active joints to measure the joint position by measuring the angular position of the associated driven link 58. In some embodiments six position sensors 112 are located at six active joints to measure an angular position of the actuators and six position sensors 112 are located at the same six active joints to measure an angular position of the links 58 being driven by the actuators. Such redundant sensor arrangements are well known in the art. Alternative embodiments of position sensor arrangements are described in U.S. Pat. No. 9,119,655, entitled, "Surgical Manipulator Capable of Controlling a Surgical Instrument in Multiple Modes," the disclosure of which is hereby incorporated by reference.

The manipulator 56 may be in the form of a conventional robotic system or other conventional machining apparatus, and thus the components thereof shall not be described in detail.

Manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers 119 (e.g., one for controlling each motor M) that control the active joints of the manipulator 56 to move the plurality of links 58 and thereby move the surgical tool 22 from the current location to the desired location.

In order to determine the current location of the surgical tool 22, data from the position sensors 112 is used to determine measured joint angles. The measured joint angles of the active joints are forwarded to a forward kinematics module, as known in the art. Based on the measured joint angles and preloaded data, the forward kinematics module determines the pose of the surgical tool 22 in a manipulator coordinate system MNPL. The preloaded data are data that define the geometry of the plurality of links 58 and joints. With this information, the manipulator controller 54 and/or navigation processor 52 can transform coordinates from the localizer coordinate system LCLZ into the manipulator coordinate system MNPL, or vice versa.

In one embodiment, the manipulator controller 54 and joint motor controllers 119 collectively form a position controller that operates to move the surgical tool 22 to commanded positions and/or orientations. The position controller operates in a position control loop. The position control loop may include multiple position control loops in parallel or series for each active joint. The position control loop processes position and orientation information to indicate and direct the pose of the surgical tool 22.

Figure 5A:
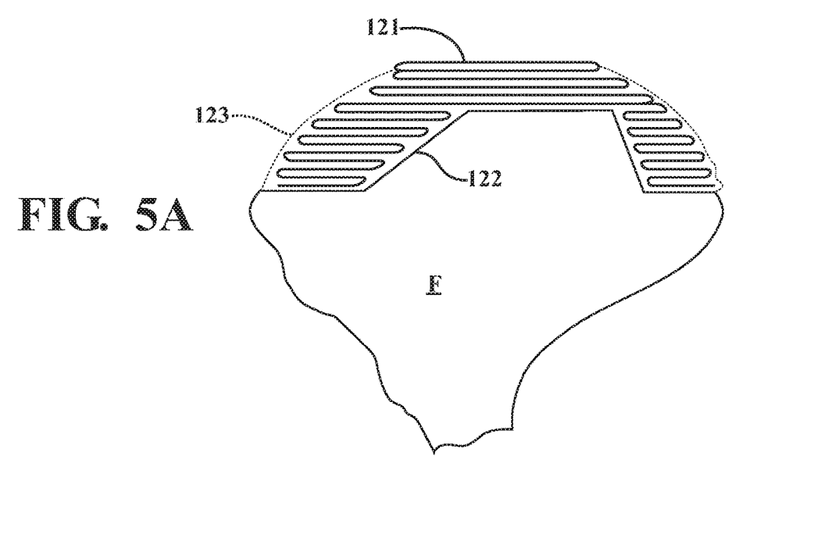
FIGS. 5A-5C are illustrations of a tool path.
Figure 5B:
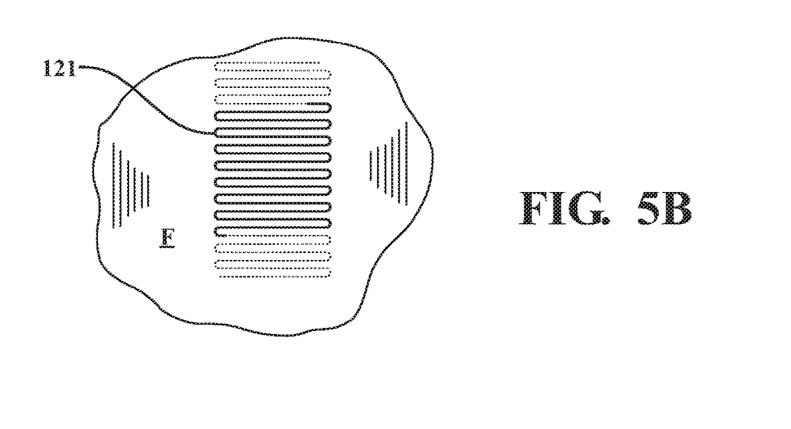

A tool path generator 120, shown in FIG. 2, is a software module that runs on the navigation processor 52. The tool path generator 120 generates a tool path 121 as seen in FIGS. 5A and 5B. FIG. 5A represents the femur F, a section of which is to be removed to receive an implant. Surface 122 is a boundary beyond which the surgical tool 22 should not be applied. The surface 122 is therefore also the outline of the femur F remaining after the removal procedure, the bone to which the implant is to be mounted. Dashed line 123 represents the perimeter of the bone that is to be removed using the manipulator 56. In FIG. 5A the tool path is represented by a back and forth line. The smoothness and quality of the finished surface depends in part on the relative positioning of the back and forth line. More specifically, the closer together each back and forth pass of the line, the more precise and smooth is the finished surface.

In addition, the configuration of the tool path 121 also contributes to the quality of the finished surface. For example, in one path configuration, the circumference of the surface boundary is cut first with the tool path migrating inward toward the center. In this configuration, there is no allowance for the outflow of the removed material. In another configuration, the tool path starts at the center of the section of bone to be removed and proceeds in an outward direction. In this way, the removed material has outflow path and does not interfere with the removal process.

In FIG. 5A the tool path 121 is shown as only being within the perimeter of the tissue being removed. The location of the tool path 121 is a function of the geometry of the distal end of the surgical tool 22. For example, the center of the distal end of the surgical tool 22 may be the origin of coordinate system EAPP. In this implementation, when the tool path 121 is generated, the tool path generator 120 accounts for the fact that the surgical tool 22 actually extends beyond the origin of coordinate system EAPP. If the surgical tool 22 is a spherical bur, this means that the tool path segments closest to boundary 122 are typically spaced away from the boundary 122 a distance at least equal to the radius of the bur head.

The tool path 121 is not plotted in a single plane. In FIG. 5B the tool path 121 is shown as comprising a number of layers wherein top most segments are shown as a set of solid connected lines and dashed lines represent segments located below the top segments.

Figure 5C:
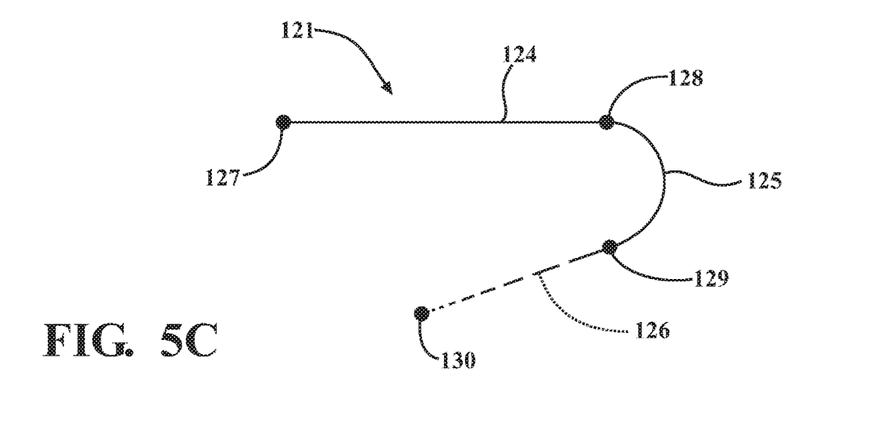

As seen in FIG. 5C, the tool path 121 includes a number of path segments. Each segment includes a set of points along which the origin of coordinate system EAPP should travel. Individual segments 124, 125, 126 may be straight or curved. Each segment 124, 125, 126 has an origin and a terminus. Point 127, is both the origin of tool path 121 and the origin of segment 124. The terminus of one segment will be the origin of the abutting segment. Thus, point 128 is both the terminus of segment 124 and the origin of segment 125. Point 129, is the terminus of segment 125 and the origin of segment 126. Point 130 is the terminus of segment 126. Point 130 may also be the terminus of tool path 121 and the origin of another tool path that is not illustrated. In FIG. 5C, segment 126 is depicted as a sequence of dashed lines, from origin to terminus, of decreasing size. This is to diagrammatically depict that the path in addition to having X and Y components, has a Z component that is into or out of the page on which FIG. 5C is depicted.

Tool path generator 120 receives as inputs the image of the tissue (e.g., image of the femur F), data defining the shape of a boundary across which the surgical tool 22 is not to extend, and surgeon's setting regarding the location of the boundary. In some implementations, the tool path generator 120 also receives as an input a solid body model of the material to be removed. In another implementation, the tool path generator 120 generates the solid body model based on the inputs of the image of the tissue, the data defining the shape of the boundary, and the surgeon settings. For an orthopedic surgical procedure, the boundary is typically the shape of the implant and the surgeon setting is often the position of the implant. Based on these data, the tool path generator 120 defines the tool path 121. Each tool path segment 124, 125, 126 is defined as a vector or a curve that extends between points present in bone coordinate system FBONE (and later transformed to the localizer coordinate system LCLZ or the manipulator coordinate system MNPL). It should be understood that the path segments are defined in three dimensions. This is because the surgical tool 22 is not just applied in a single plane to the tissue. The surgical tool 22 also moves up or down in order to contact tissue in the plane above or below the plane in which it is presently located.

Figure 6:
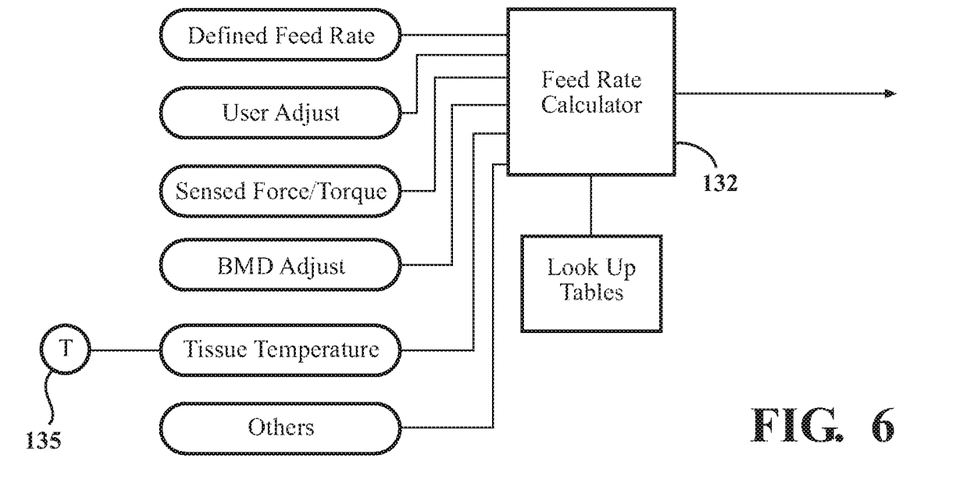
FIG. 6 is a schematic view of a feed rate calculator and inputs into the feed rate calculator.

A feed rate calculator 132, shown in FIGS. 2 and 6, is a software module that runs on the manipulator controller 54. The feed rate calculator 132 determines the velocity, referred to as the tool feed rate, at which the distal end of the surgical tool 22 should move as it travels along an individual path segment. The primary input into the feed rate calculator 132 is the defined feed rate. In practice, the manipulator controller 54 is often provided with plural defined feed rates. A specific defined feed rate is assigned to each path segment of the tool path 121 along which the surgical tool 22 is programmed to traverse. This feed rate assignment may be performed preoperatively. The feed rates can then be adjusted at the start of or during the procedure. Two or more contiguous path segments may be assigned the same defined feed rate. These feed rates are generated based on variables such as: the shape of the material to be removed by the surgical tool 22; the type of energy applicator of the surgical tool 22; the health of the patient; the nature of the tissue to which the surgical tool 22 is applied; and the geometry of the path segment. In practice, the defined feed rate is typically between 5 and 400 mm/sec.

The feed rate calculator 132 adjusts the defined feed rate to produce the tool feed rate. In one version, this adjustment is performed by multiplying the defined feed rate by a number of coefficients. Each coefficient is generally between 0 and 1.0. Coefficients may have values that exceed 1.0. Each of these coefficients changes as a function of a variable that is also applied to the feed rate calculator 132. In practice, there may be several different coefficients used to produce the tool feed rate. Several such coefficients are described in detail in U.S. Pat. No. 9,119,655, entitled, "Surgical Manipulator Capable of Controlling a Surgical Instrument in Multiple Modes," the disclosure of which is hereby incorporated by reference.

A first variable used to adjust the defined feed rate includes a user adjustment of the feed rate. This is the adjustment of the feed rate that the practitioner performs, in real time, as the procedure progresses. The practitioner makes this adjustment of the feed rate by depressing buttons 133 and 134 of a user control pendant 142 shown in FIG. 1. The feed rate calculator 132 outputs a coefficient as a function of the practitioner entered command to increase or decrease the tool feed rate.

A second variable used to selectively scale the defined feed rate is force and torque to which the surgical tool 22 is exposed. The surgical tool 22 is rigidly attached to the manipulator 56. Accordingly, signals output by a force/torque sensor 108 located between the surgical tool 22 and the manipulator 56 are the signals representative of the forces and torques to which surgical tool 22 is exposed. Feed rate calculator 132 sets the tool feed rate based on the principle that there is a relationship between the amount of force/torque that the manipulator 56 applies to the surgical tool 22 and the rate of tool advancement. Generally, it is a goal of modern medical practice to minimize the heating of tissue that is not being removed. One reason for this goal is to minimize the attendant damage this needless heating can cause to the tissue. Accordingly, manipulator 56 is configured to, when it is determined that an appreciable amount of force and/or torque is applied to the surgical tool 22, slow the advancement of the surgical tool 22 along the path segment.

One example of where this adjustment of the tool feed rate is useful is when the surgical tool 22 travels across a path segment through both cortical bone and cancellous bone. Cortical bone, the outer bone, is relatively hard. Cancellous bone, the inner bone, is more porous and less resistant to removal than cortical bone. Accordingly if the surgical tool 22 moves across both types of bone at a constant speed, more force/torque is needed to be applied to move the energy applicator across the cortical bone than the cancellous bone. This means that, without adjustment of tool speed, the cortical bone would be subject to more potentially damage inducing heating than the adjacent section of cancellous bone. This feature of the manipulator 56 minimizes this potential for the unwanted heating by slowing the rate of advancement for the surgical tool 22 when the force/torque sensor 108 provides signals indicating that the amount of force/torque required to advance the surgical tool 22 increases.

Once the surgical tool 22 moves from cutting the cortical bone to cancellous bone, the force/torque required to advance the surgical tool 22 decreases. In this situation, the rate at which the surgical tool 22 is advanced can be speeded up without appreciably increasing the extent to which the bone is heated. The feed rate calculator 132 therefore increases the calculated rate of the advancement of the surgical tool 22. This reduces the amount of time it takes to perform the procedure on the patient. This is desirable because it is a further goal of modern surgical practice to minimize the time it takes to perform the procedure on the patient. One reason this time minimization is desired is because it lessens the amount of time the patient's internal tissue is exposed and open to infection. Also, performing the procedure as quickly as possible lessens both the likelihood of surgeon fatigue and the amount of time the patient must be held under anesthesia.

The feed rate calculator 132 determines a force/torque adjustment coefficient as based on one, two or three of: (1) the magnitude of a six component vector comprised of the individual force and torque components; (2) the magnitude of a three component vector comprised of the individual force components; and (3) the magnitude of a vector comprised of any combination of individual force and/or torque components. Alternatively, the coefficient is based on one or more of the largest force or torque components. Based on one or more of these variables, the feed rate calculator 132, by reference to data in an associated look-up table, determines a force/torque adjustment coefficient.

A third variable for adjusting the defined feed rate is a bone mineral density (BMD) coefficient. The BMD coefficient is based on the BMD of the material being removed by the surgical tool 22. Most of the time, the material being removed by the surgical tool 22 is non-homogenous with respect to BMD. Accordingly, in order to determine this coefficient, a BMD distribution first needs to be established for the bone to which the surgical tool 22 is to be applied. For example, if the surgical tool 22 is being used to remove material from the femur F and tibia T, separate BMD distributions should be determined for each of the femur F and tibia F. The BMD distribution may be determined pre-operatively or intraoperatively.

BMD measuring systems and methods for determining BMD distributions for volumes of bone are known in the art. One example of a BMD measuring system and method is described in "VISBONE: 3D Visualization of Bone Mineral Density" by Choi et al. from the Pacific Conference on Computer Graphics and Applications, pages 138-146, IEEE Computer Society, (1999), hereby incorporated by reference. The densities measured by this BMD measuring system and method may be expressed in $g/cm^3$. BMD may also be determined using Quantitative Computed Tomography (QCT), which uses a standard Computed Tomography (CT) scanner with a calibration standard to convert Hounsfield Units (HU) of the CT image to BMD values.

The BMD distribution is provided as part of a 3-D representation or model of the bone that is generated by the BMD measuring system and stored in memory in the navigation computer 26 and/or the manipulator controller 54. The 3-D representation may comprise a plurality of voxels with the number of voxels being based on the desired resolution of the 3-D model. Point clouds with associated BMD values or other suitable BMD distribution methods may be employed. Each voxel in the 3-D model is assigned a density based on the measurements taken of the particular bone. The 3-D model is registered to the actual bone, such as the femur F, so that as the bone moves during the surgery, the 3-D model also moves and is tracked by the guidance station 20 so that the material removal system 10 is able to track the location of the working end of the surgical tool 22 relative to the bone and relative to the voxels containing the density data.

The BMD coefficient may be predetermined and stored in a look up table in memory in the navigation computer 26 and/or manipulator controller 54 that associates BMD coefficients to each voxel in the 3-D model. So, each time the tool feed rate is calculated, the feed rate calculator 132 receives as an input a BMD coefficient from the look up table. The corresponding BMD coefficient in the look up table is the one associated with the particular voxel in which the working end of the surgical tool 22 is virtually and currently located. The BMD coefficients may include 0.2, 0.4, 0.6, 0.8, 1.0 or other variations of coefficients from 0.0 to 1.0. The BMD coefficients generally decrease as the BMD increases. There may be ranges of densities associated with each particular coefficient. The densities for different clusters of adjacent voxels may also be averaged to determine a common BMD coefficient for each of the different clusters. The BMD coefficients may be determined based on the range of densities measured in the BMD distribution with the highest density receiving a BMD coefficient of 0.1 and the lowest density receiving a BMD coefficient of 1.0, and all other densities therebetween receiving a linearly interpolated BMD coefficient between 0.1 and 1.0.

The BMD coefficient takes into account that the tool feed rate should be set relatively slower when the surgical tool 22 encounters denser material, such as cortical bone. It may be desirable in denser bone to have a slower tool feed rate in order to maintain consistent cutting accuracy. Otherwise, if the tool feed rate is set too high, errors may occur as a result of unexpected deflections of the surgical tool 22, which may yield inaccurate cuts. Conversely, for less dense bone, such as cancellous bone, relatively faster tool feed rates may be appropriate, resulting in quicker operating times, while maintaining desired cutting accuracy. The feed rate calculator 132 therefore increases the calculated rate of advancement of the surgical tool 22. As a result, the tool feed rate is able to be changed between portions of bone or other materials having different densities. This reduces the amount of time it takes to perform the procedure on the patient to further the goal of minimizing the time it takes to perform the procedure on the patient.

In some embodiments, the tool path generator 120 may also generate the tool path 121 based on the BMD distribution. For instance, it may be desired to first remove all material having a density higher than a predetermined density threshold. In such a case, the tool path 121 may be defined to first remove the denser material in thinner layers, while less dense material is then removed in relatively thicker layers, or vice versa. This may further increase the efficiency of the material removal system 10 thereby further reducing procedure times.

In one embodiment, in order to generate the tool path 121 based on the BMD distribution, the tool path generator 120 first evaluates the BMD distribution by retrieving the BMD coefficients from each voxel in the 3-D model and classifying each of the voxels as being low density (one example of a density classification) or high density (another example of a density classification) based on a predefined threshold (e.g., high is at or above the threshold and low is below the threshold, with the threshold being any desired value). The tool path generator 120 then generates a first section of the tool path 121 to cut high density material and a second section of the tool path 121, following the first section, to cut low density material, or vice versa. For situations in which all the high density material is not contiguous, but is bridged by low density material, the tool path generator 120 may be configured to save those portions of material for later sections of the tool path so that the largest volume of contiguous portions of high density material is cut first, then the largest volume of contiguous portions of low density material is cut, and finally the remaining portions are cut.

The tool path 121 may also be split into different levels of tool paths so that this procedure is followed for a first level of material independently of a second level below the first level, and so on. The different levels may have a depth (thickness) equal to the diameter of the surgical tool 22, such as the bur head. Accordingly, after each level of material is removed based on the BMD distribution for that level, the procedure resets for the next lower level. This may be especially helpful when contiguous portions of high density material are found below portions of low density material, and thus cannot be reached by the surgical tool 22 until the material above it is removed.

The tool path 121 may also be altered along each path segment based on the density of material for that particular path segment. For instance, a new path segment may be configured so that the surgical tool 22 cuts deeper into the remaining material when the density is lower when compared to a previous path segment. Accordingly, more material can be removed in a shorter amount of time by cutting more material when possible, i.e., whenever lower density material is found. Conversely, the new path segment may be configured so that the surgical tool cuts a shallower path into the remaining material when the density is higher as compared to a previous path segment. This tool path generation could be based on a segment-by-segment basis, or multiple, different tool paths could be created in which the depth of cutting of one tool path is greater than a depth of cutting of an adjacent tool path. As a result, sculpting of the workpiece to remove the material may be stepwise in accordance with the BMD distribution.

Figure 7:
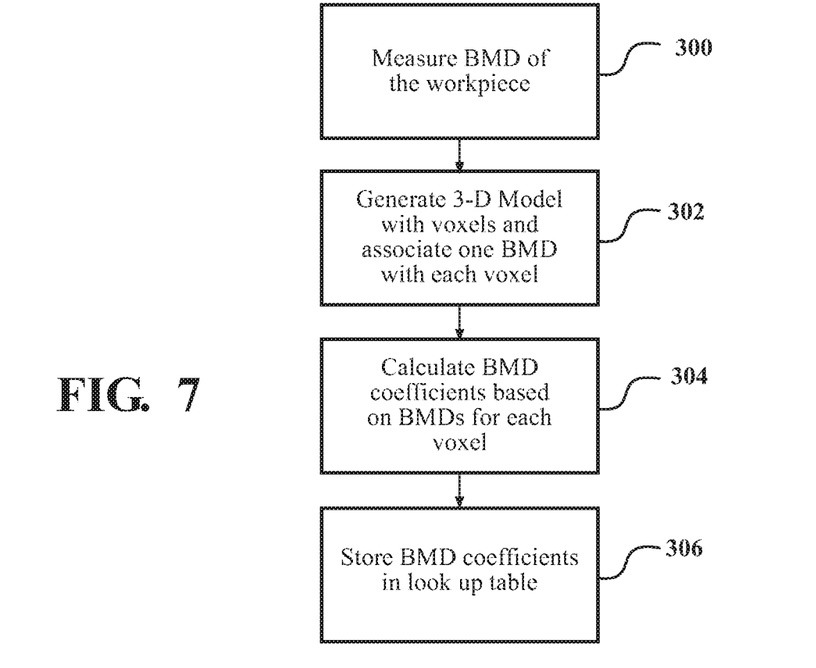
FIGS. 7 and 8 are flow charts of steps carried out by a method for removing material from the workpiece.
Figure 8:
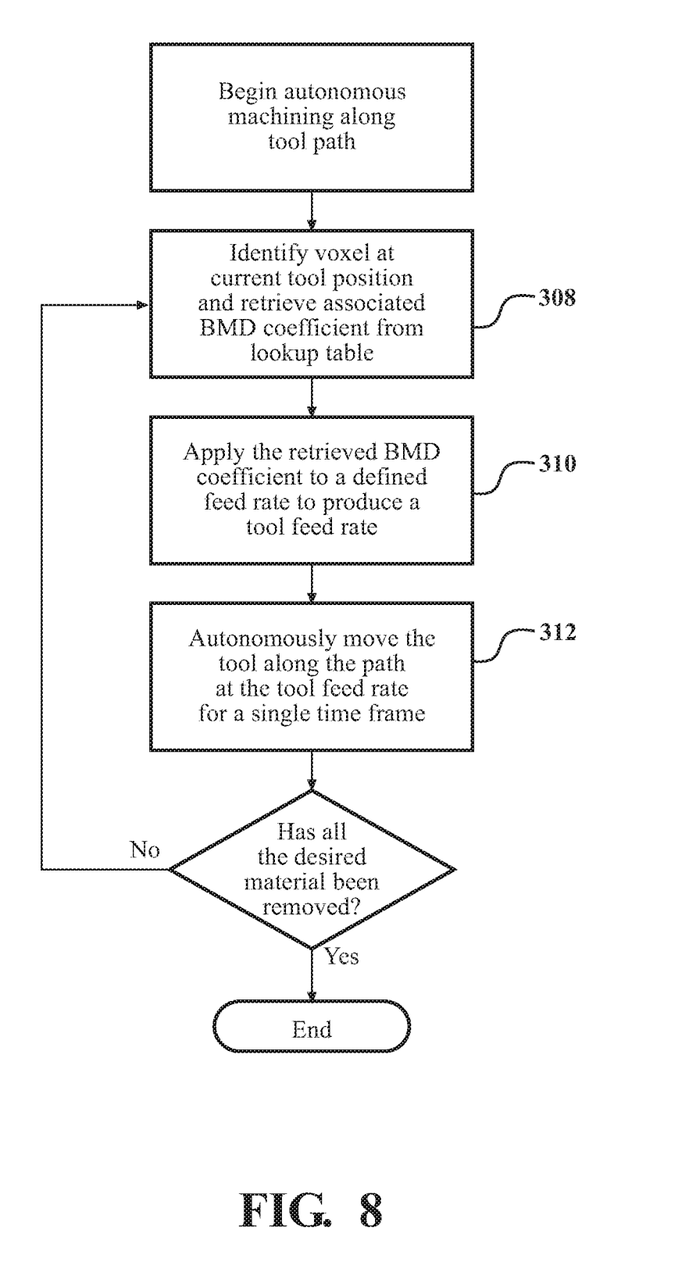

FIGS. 7 and 8 illustrate a series of steps carried out in one embodiment in order to determine the BMD coefficient. In step 300, the BMD of the workpiece, such as the femur F is first measured using BMD measuring systems described above. These same systems generate a 3-D model of the workpiece in step 302 with the 3-D model being broken down into a plurality of voxels. A BMD from the BMD distribution is associated with each of the plurality of voxels. The BMDs may be associated by look up table, by attributing BMD data to coordinates of the 3-D model directly, etc.

In step 304, BMD coefficients are calculated in the manner previously described based on the measured BMD for each voxel, group of voxels, etc. The BMD coefficients may range anywhere from 0.0 to 1.0, and in some cases may be higher than 1.0. A BMD coefficient higher than 1.0 may be desired in situations where the encountered BMD is extremely low and efficiency of the procedure requires increasing the tool feed rate to a rate higher than the defined feed rate. The BMD coefficients are then stored in a look up table for access by the feed rate calculator 132 in step 306.

Once the BMD coefficients are determined and stored in the look up table, the material removal system 10 identifies, in step 308, the particular voxel in which the surgical tool 20 is currently positioned based on the position and orientation data from the guidance station 20. The associated BMD coefficient is then retrieved from the look up table and provided as an input to the feed rate calculator 132.

In step 310, the associated BMD coefficient is then applied to the defined feed rate (e.g., a default feed rate for the particular procedure) by the feed rate calculator 132 to produce a tool feed rate by multiplying the defined feed rate by the BMD coefficient (other coefficients may or may not be used in this embodiment). For instance, if the defined feed rate is 100 mm/sec and the BMD coefficient is 0.5, then the tool feed rate is set to 50 mm/sec by the feed rate calculator 132.

Once the tool feed rate is set, the manipulator controller 54 instructs the joint motor controllers 119 in step 312 to operate in a manner that autonomously moves the surgical tool 22 along the tool path 121 at the tool feed rate. Steps 308 through 312 are repeated until all the material to be removed from the workpiece has been removed, or until an error occurs requiring the material removal system 10 to stop movement of the surgical tool 20.

A fourth variable that is used as a factor for adjusting the defined feed rate to produce the tool feed rate is tissue temperature. This is due to the above mentioned goal of modern surgical practice to minimize the extent that the patient's uncut tissue is heated. Temperature sensor 135 provides an indication of the tissue temperature. Typically, the sensor 135 is mounted to the surgical tool 22. Again, the signal output by the sensor 135 may be representative of the temperature of the tissue or the temperature of the working end of the surgical tool 22, e.g., the bur. Often the signal output by the sensor 135 is routed through tool controller 138 to the manipulator controller 54. In addition to the temperature of the uncut tissue, another factor for adjusting the defined feed rate may include the temperature of the chips removed by the surgical tool 22. The chips and material removed are often referred to as "slurry." The temperature of the slurry may be measured in any suitable manner including the sensor 135.

The feed rate calculator 132, based on the temperature represented by the tissue temperature signal and by reference to one of the look-up tables, determines the appropriate tissue temperature feed rate adjustment coefficient. If the tissue temperature signal indicates that the tissue temperature is within an acceptable range, this coefficient may be at or near 1.0. Alternatively, if the tissue temperature signal indicates that the tissue or surgical tool 22 temperature is approaching or above a level at which there may be appreciable damage to the tissue, the retrieved coefficient may decrease from unity.

The feed rate calculator 132 multiplies the defined feed rate by the above coefficients and/or others as defined in U.S. Pat. No. 9,119,655, entitled, "Surgical Manipulator Capable of Controlling a Surgical Instrument in Multiple Modes," the disclosure of which is hereby incorporated by reference. The product of this process is the tool feed rate. This is the rate at which the working end of the surgical tool 22 should be advanced along the current path segment. The feed rate calculator 132 may perform this calculation to reset the tool feed rate for each time frame in which target positions for the working end of the surgical tool 22 are determined by the manipulator controller 54, as described below. In some versions, the period of a time frame is 0.1 to 2 milliseconds. In other embodiments, the tool feed rate may be held constant over two or more time frames.

There is no requirement that in all embodiments the feed rate calculator 132 always calculate the tool feed rate based on the instantaneous values of the variables. In some versions, these input variables may be filtered. Likewise, there may be reasons to vary the coefficients that are used as the multipliers to establish the extent any variable effects feed rate. The application of a particular variable may be delayed. The varying of the coefficient may be filtered or ramped to blend in/out the effect of the change in the magnitude of the coefficient. This filtering or blending results in a smoothing out of the advancement of the surgical tool 22. This smoothing out of the advancement of the surgical tool 22 may reduce the likelihood that, owing to rapid changes in the positioning of the surgical tool 22, the manipulator 56 may become unstable or overshoot the target position. The effect of any variable may be selectively disregarded. For example, when the BMD coefficient is utilized to adjust the tool feed rate, the force/torque adjustment coefficient may be disregarded. The BMD coefficient is determined independently of any force/torque acting on the surgical tool 22, but the force/torque adjustment coefficient inherently accounts for differences in material density based on the nature of such materials. It may also be desirable to only generate the tool feed rate based on either the smallest or largest coefficient, while the other coefficients are disregarded.

In some embodiments, two or more variables into feed rate calculator 132 may be combined. This combining may be by summing, multiplying, averaging or dividing. The calculated coefficients may likewise be summed, multiplied, averaged or divided to provide a final coefficient used to, based on the defined feed rate, establish the tool feed rate.

Likewise, there is no requirement that the coefficients may be determined solely on the basis of a variable-to-coefficient feed rate table. Other means to determine these coefficients are based on using the variables as input variables into an equation the result of which is the coefficient used to establish the tool feed rate. The equations may be polynomial equations or non-linear equations.

In addition to adjusting the feed rate and/or the tool path, the rotational speed of the surgical tool 22 may also be varied based on the BMD distribution or other factors. The rotational speed of the surgical tool 22 is controlled by the tool controller 138.

When the surgical tool 22 includes a bur, the speed of rotation of the cutting teeth of the bur may be adjusted and optimized to improve the accuracy of the tissue removal and to minimize heat generation at the tissue. The optimal speed of the bur cutting teeth is a factor of cutter rotational speed and cutter diameter, which are optimized based on the tooth geometry and the type of material being removed. In cases where the material being cut is increasing or decreasing in density, the rotational speed of the surgical tool 22 may be adjusted to reduce heat generation while the surgical tool 22 is moving relative to the material being removed based on the desired feed rate. The rotational speed may also be adjusted in proportion to the feed rate adjustment. For instance, the faster the feed rate, the faster the rotational speed of the surgical tool 22. While the slower the feed rate, the slower the rotational speed of the surgical tool 22, or vice versa.

In some cases, experimental data associated with preferred cutting speeds based on bone density may be used to control the rotational speed of the surgical tool 22. Accordingly, a look-up table may be employed to determine the appropriate rotational speed for a particular density of material encountered during cutting. The look-up table may be stored in the memory of the navigation computer 26 and/or manipulator controller 54 and the appropriate rotational speed may be output by the navigation computer 26 or the manipulator controller 54 to the tool controller 138 based on the density of the material being encountered to control the rotational speed of the surgical tool 22 accordingly.

The rotational speed may be controlled in real-time, i.e., for each time frame in which target positions for the working end of the surgical tool 22 are determined by the manipulator controller 54, as described below. In some versions, the period of a time frame is 0.1 to 2 milliseconds. In other embodiments, the rotational speed may be held constant over two or more time frames. The rotational speed may also be reset for each path segment of the tool path, so a constant rotational speed for each path segment would be set and then adjusted for the next path segment, if needed. Alternatively, the rotational speed may be reset for each new tool path.

A path interpolator 140, seen in FIG. 2, is a software module that runs on the manipulator controller 54. The path interpolator 140 determines the target positions for the working end of the surgical tool 22. These target positions are points along which the distal end of energy applicator 184 should travel to perform the desired task. Inputs into the path interpolator 140 include: the data defining the origin and terminus of a path segment; the data indicating if the segment is straight or curved and, if curved, the characteristics of the curve. Another input into the path interpolator 140 is the tool feed rate from feed rate calculator 132. This is the rate at which the surgical tool 22 should travel along the path segment as determined by the feed rate calculator 132.

Based on the above input variables, the path interpolator 140 determines the target position of the working end of the surgical tool 22 according to the following steps:

1) An initial position is determined, which is a position along the path segment over which the surgical tool 22 should travel. For example, if the surgical tool 22 is at the beginning point 127 of the path segment 124, this point is the initial position.

2) Based on the tool feed rate, the distance along which the surgical tool 22 would travel along the path segment in a single time frame is calculated. In some versions, the period of a time frame is 0.1 to 2 milliseconds.

3) Based on the initial position, the length of the calculated distance and the location of the segment terminus, path interpolator 140 generates data defining the target position. A further variable used to determine target positions are data from the tool path generator 120 describing the characteristics of the path segment: straight or curved; and, if curved, the radius of curvature.

4) Steps 1 through 3 are repeated until it is determined that the surgical tool 22 has reached the terminus of the path segment. After the calculation of the first target position spaced from the segment origin, the target position calculated in each frame is employed as the initial position upon which the calculation of the next frame's target position is based.

5) Once the target position equals the terminus position for a path segment, interpolator 140 repeats steps 1 through 4 to generate a set of target positions that are located along the new segment.

During the time period of a single frame, the distance the surgical tool 22 is able to travel may be greater than the distance to the terminus position for the current segment. If the path interpolator 140 determines that the surgical tool 22 would be in this state, the interpolator 140, for a time point starting when it is determined that the working end of the surgical tool 22 would be at the terminus of the current path segment, generates data indicating where the working end of the surgical tool 22 should be located along the next path segment at the end of that frame.

Once the practitioner is ready to begin autonomous advancement of the surgical tool 22, the practitioner depresses button 134 (see FIG. 1). In some versions, based on the depression of buttons 133 and 134, a coefficient representative of the user adjustment of the feed rate is transmitted from a pendant controller 144 associated with the user control pendant 142 to the manipulator controller 54. The pendant controller 144 may have a central processing unit (CPU) and/or other pendant processors, memory (not shown), and storage (not shown). The pendant controller 144 is in communication with the manipulator controller 54. The pendant controller is also in communication with switches (not shown) associated with buttons 133 and 134. The pendant processors could include one or more processors to transmit signals resulting from pressing of buttons 133 and 134 on the user control pendant 142 to the manipulator controller 54 and/or to convert the pressing of the buttons 133 and 134 into the coefficients representative of the user adjustment of the feed rate. The processors can be any type of microprocessor or multi-processor system. The term processor is not intended to limit any embodiment to a single processor.

In some versions, the coefficient is 0.0, 0.25, 0.40, 0.70 or 1.0. This is the coefficient that is applied to feed rate calculator 132 as the user adjustment input. Each depression of pendant button 133 results in the pendant controller 144 readjusting the feed rate coefficient down a level. Each depression of pendant button 134 results in the pendant controller 144 readjusting the feed rate coefficient up to the next higher level. Pendant controller 144 continually monitors the user control pendant 142 to determine whether or not either of buttons 133 or 134 is depressed.

The initial depression or depressions of button 134 causes the pendant controller 144 to upwardly adjust the level of the user adjustment coefficient applied to the feed rate calculator 132. The level to which this coefficient is set is a function of the number of times button 134 is pulsed. The feed rate calculator 132, in response to receipt of this non-zero coefficient, outputs a non-zero tool feed rate. This assumes that none of the other coefficients applied to feed rate calculator 132 are zero. Based on this indication that the surgical tool 22 is to advance at a non-zero speed, manipulator controller 54 cooperates to output signals to the joint motor controllers 119 to cause the advancement of the surgical tool 22 along the tool path 121.

In some embodiments, the manipulator 56 is a robotic surgical cutting system for cutting away material from a patient's anatomy, such as bone or soft tissue. The cutting system cuts away material to be replaced by surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation," the disclosure of which is hereby incorporated by reference. The guidance station 20 instructs the surgeon on proper procedures for locating these implants on bone and securing the implants in position, including the use of trial implants.

In alternative embodiments the trackers 44, 46, 48 could be other line-of-sight tracking devices or non line-of-sight tracking devices used for navigation. The trackers 44, 46, 48 could employ sound waves, magnetic fields, RF signals, and the like to determine position and/or orientation.

The term "memory" is intended to include memory associated with a processor such as a CPU, and may include, for example, RAM (random access memory), ROM (read only memory), a fixed memory device (for example, hard drive), a removable memory device (for example, diskette), a flash memory and the like.

As will be appreciated by one skilled in the art, aspects of the present invention may take the form of a computer program product embodied in one or more computer readable medium(s) having computer readable program code embodied thereon. Computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of operating a robotic system including a manipulator, a tool coupled to the manipulator to remove material from a workpiece, a manipulator controller coupled to the manipulator, and a navigation computer, wherein the workpiece includes a density distribution of material determined from a three-dimensional representation of the workpiece that includes a plurality of points or voxels, said method comprising:
- evaluating with the navigation computer the density distribution by classifying the plurality of points or voxels into a first density classification and a second density classification different than the first density classification;
- thereafter, with the navigation computer:
  - identifying a first portion of the material derived from the first density classification;
  - generating a first tool path for the tool for a first level of the material, the first tool path having a configuration enabling the tool to remove the first portion of the material;
  - identifying a second portion of the material derived from the second density classification; and
  - generating a second tool path for the tool for a second level of the material below the first level of the material, the second tool path having a configuration enabling the tool to remove the second portion of the material;
- tracking with the navigation computer a position of the tool relative to the workpiece as the tool moves relative to the workpiece; and
- controlling with the manipulator controller the position of the tool relative to the workpiece to remove at least a portion of the material along the first tool path; and
- thereafter, controlling with the manipulator controller the position of the tool relative to the workpiece to remove at least a portion of the material along the second tool path.

2. The method of claim 1, wherein the step of evaluating the density distribution further comprises classifying the plurality of points or voxels into the first and second density classifications relative to a predetermined density threshold, wherein the points or voxels classified into first density classification are above the predetermined density threshold, and the points or voxels classified into the second density classification are below the predetermined density threshold.

3. The method of claim 1, further comprising:
- assigning a density coefficient to each of the plurality of points or voxels in the three-dimensional model based on measurements taken of the workpiece; and
- comparing the assigned density coefficients for each of the plurality of points or voxels to a predetermined density threshold.

4. The method of claim 3, further comprising averaging assigned density coefficients from adjacent points or voxels to determine a common density coefficient for a cluster of the points or voxels.

5. The method of claim 1, wherein the first tool path includes a plurality of contiguous tool path segments, wherein said method further comprises altering the first tool path between the tool path segments based on the evaluated density distribution for the respective tool path segments.

6. The method of claim 5, further comprising generating the first tool path for each of the tool path segments as the tool moves relative to the workpiece.

7. The method of claim 5, wherein the tool path segments are vector or curves that extends between the plurality of points or voxels.

8. The method of claim 1, wherein the first density classification is indicative of denser material relative to the second density classification being indicative of less dense material, and wherein the denser material is located within two noncontiguous regions separated by a region of the less dense material, wherein said method further comprises:
- controlling the position of the tool to remove a first of the two noncontiguous regions of the denser material and the region of the less dense material; and
- thereafter, controlling the position of the tool to remove a second of the two noncontiguous regions of the denser material.

9. The method of claim 8, where the two noncontiguous regions of the denser material are of different volumes, wherein said method further comprises:
- controlling the position of the tool to remove a larger volume of the two noncontiguous regions of the denser material; and
- thereafter, removing a smaller volume of the two noncontiguous regions of the denser material.

10. The method of claim 1, further comprising assigning or adjusting a feed rate of the tool preoperatively or intraoperatively.

11. The method of claim 1, wherein the step of generating with the navigation computer the second tool path is performed after the material is removed along the first tool path.

12. The method of claim 1, wherein the first level and the second level have a depth equal to a diameter of the tool.

13. The method of claim 1, further comprising:
- controlling with the manipulator controller the position of the tool relative to the workpiece to remove the material along the first tool path at a first cutting depth; and
- controlling with the manipulator controller the position of the tool relative to the workpiece to remove the material along the second tool path at a second cutting depth greater than the first cutting depth based on the second density classification being indicative that the second portion of the material is less dense than the first portion of the material of the first density classification.

14. A robotic system for removing material from a workpiece having a density distribution of material determined from a three-dimensional representation of the workpiece that includes a plurality of points or voxels, the robotic system comprising:
- a manipulator;
- a tool coupled to the manipulator to remove the material from the workpiece;
- a manipulator controller coupled to the manipulator and configured to control a position of the tool relative to the workpiece; and
- a navigation computer in communication with the manipulator controller and configured to track a position of the tool relative to the workpiece,
- wherein the navigation computer is configured to:
  - evaluate the density distribution by classifying the plurality of points or voxels into a first density classification and a second density classification different than the first density classification;
  - thereafter, generate a first tool path for the tool for a first level of the material based on the evaluated density distribution of the workpiece and associated with the first density classification; and
  - thereafter, generate a second tool path for the tool for a second level of the material below the first level of the material, the second tool path based on the evaluated density distribution and associated with the second density classification,
- wherein the manipulator controller is configured to:

control the position of the tool relative to the workpiece to remove at least a portion of the material along the first tool path; and thereafter, control the position of the tool relative to the workpiece to remove at least a portion of the material along the second tool path.

15. The robotic system of claim 14, wherein the manipulator controller is further configured to control the position of the tool to remove the material along the first tool path prior to removing the material along the second tool path.

16. The robotic system of claim 14, wherein the first tool path includes a plurality of contiguous tool path segments, wherein the navigation computer is further configured to alter the first tool path between the tool path segments based on the evaluated density distribution for the respective tool path segments.

17. The robotic system of claim 16, wherein the navigation computer is further configured to alter the first tool path for each of the tool path segments as the tool moves relative to the workpiece.

18. The robotic system of claim 16, wherein the tool path segments are vector or curves that extends between the plurality of points or voxels.

19. The robotic system of claim 14, wherein the first density classification is representative of denser material relative to less dense material represented by the second density classification, and wherein the denser material is located within two noncontiguous regions separated by a region of the less dense material, wherein the manipulator controller is further configured to control the position of the tool to remove a first of the two noncontiguous regions of the denser material and the region of the less dense material prior to removing a second of the two noncontiguous regions of the denser material.

20. The robotic system of claim 19, where the two noncontiguous regions of the denser material are of different volumes, wherein the manipulator controller is further configured to control the position of the tool to remove a larger volume of the two noncontiguous regions of the denser material prior to removing a smaller volume of the two noncontiguous regions of the denser material.

* * * * *